(12) United States Patent
Brechbiel et al.

(10) Patent No.: US 7,081,452 B2
(45) Date of Patent: Jul. 25, 2006

(54) SCORPIONATE-LIKE PENDANT MACROCYCLIC LIGANDS, COMPLEXES AND COMPOSITIONS THEREOF, AND METHODS OF USING SAME

(75) Inventors: Martin W. Brechbiel, Annandale, VA (US); Hyun-Soon Chong, Chevy Chase, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 386 days.

(21) Appl. No.: 10/318,821

(22) Filed: Dec. 13, 2002

(65) Prior Publication Data

US 2003/0228262 A1 Dec. 11, 2003

Related U.S. Application Data

(60) Provisional application No. 60/385,371, filed on Jun. 3, 2002.

(51) Int. Cl.
*A61K 31/33* (2006.01)
*A61P 35/00* (2006.01)
*C07D 245/00* (2006.01)

(52) U.S. Cl. ............... 514/183; 540/460; 424/9.3; 424/9.32; 424/9.363; 424/9.42; 424/9.44; 534/10; 534/13; 534/14; 534/16

(58) Field of Classification Search ......... 514/183; 540/460; 424/9.3, 9.32, 9.363, 9.42, 9.44; 534/10, 13, 14, 16
See application file for complete search history.

(56) References Cited

FOREIGN PATENT DOCUMENTS

WO WO95/19347 7/1995

OTHER PUBLICATIONS

Bambirra et al., *Chem. Commun.*, 637-638 (Mar. 14, 2001).
Berreau et al., *Inorg. Chem.*, 37, 1091-1098 (1998).
Cox et al., *J. Chem. Soc., Perkin Trans. 1*, 2567-2576 (1990).
Curtis et al., *J. Chem. Soc. A.*, 1015-1018 (1966).
Fortier et al., *J. Chem. Soc. Dalton Trans.*, 101-109 (1991).
Hnatowich et al., *Science*, 220, 613-615(1983).
Kovacs et al., *Synth. Commun.*, 29(16), 2817-2822 (1999).
Krejcarek et al., *Biochem. Biophys. Res. Commun.*, 77(2), 581-585 (1977).
Male et al., *Inorg. Chem.*, 39, 5483-5491 (2000).
McMurry et al., *Bioconjugate Chem.*, 3, 108-117 (1992).
Pletnev, *Can. J. Chem.*, 72(4), 1404-1411 (1994).
Renn et al., *Bioconjugate Chem.*, 3, 563-569 (1992).
Rossi et al., *Tetrahedron Letters*, 39, 7159-7162 (1998).
Tei et al., *J. Chem. Soc. Dalton Trans.*, 2793-2799 (2000).
Warden et al., *Org. Lett.*, 3(18), 2855-v2858 (Aug. 15, 2001).
Weisman et al., *J. Org. Chem.*, 61, 5186-5187 (1996).
Chong et al., *J. of Medicinal Chemistry*, 45(16), 3458-3464 (2002).

*Primary Examiner*—Brenda Coleman
(74) *Attorney, Agent, or Firm*—Leydig, Voit & Mayer, Ltd.

(57) ABSTRACT

Substituted 1,4,7-triazacyclononane-N,N',N"-triacetic acid compounds with a pendant donor amino group, metal complexes thereof, compositions thereof, and methods of use in diagnostic imaging and treatment of a cellular disorder.

63 Claims, 3 Drawing Sheets

SCORPIONATE-LIKE PENDANT MACROCYCLIC LIGANDS, COMPLEXES AND COMPOSITIONS THEREOF, AND METHODS OF USING SAME

CROSS-REFERENCE TO RELATED PATENT APPLICATIONS

This patent application claims the benefit of U.S. Provisional Patent Application No. 60/385,371, filed Jun. 3, 2002.

FIELD OF THE INVENTION

This invention pertains to substituted 1,4,7-triazacyclononane-N',N'',N'''-triacetic acid compounds with a pendant donor amino group, metal complexes thereof, compositions thereof and methods of using same.

BACKGROUND OF THE INVENTION

Monoclonal antibodies (mAbs) have been employed as targeting biomolecules for the delivery of radionuclides into tumor cells in radioimmunotherapy (RIT). Numerous clinical trials have been performed to validate this modality of cancer therapy (see, for example, Parker et al., *Pure Appl. Chem.*, 1991, 63, 427–463; Chakrabarti et al., *J. Nuc. Med.*, 1996, 37, 1384–1388; Sharkey et al., *Cancer Res.*, 1988, 48, 3270–3275; Sharkey et al., *Cancer Res.*, 1988, 48, 3270–3275; and Lee et al., *Cancer Res.*, 1990, 50, 4546–4551). Several useful β⁻-emitting radionuclides, including $^{131}$I, $^{90}$Y, $^{177}$Lu, and $^{153}$Sm, have been employed for labeling mAbs for RIT applications (Denardo et al., *Cancer*, 1994, 73, 1012–1022; Scott et al., *Cancer*, 1994, 73, 993–998; Schlom et al., *Cancer Res.*, 1991, 51, 2889–96).

The pure β⁻-emitting radionuclide $^{90}$Y ($E_{max}$=2.28 MeV; $t_{1/2}$=64.1 h) has been extensively studied in RIT due to its physical properties (see, for example, Martell et al., *Critical Stability Constants*, Vol. 1: Amino Acids. Plenum Press: New York, 1974; pp. 281–284; Wessels et al., *Med Phys.*, 1984, 11, 638–645; Chinol et al., *J. Nucl. Med.*, 1987, 28, 1465–1470; and Mausner et al., *Med Phys.*, 1993, 20, 503–509). The macrocyclic chelating agent 1,4,7,10-tetraazacyclododecane-N,N',N'',N'''-tetraacetic acid ("DOTA")

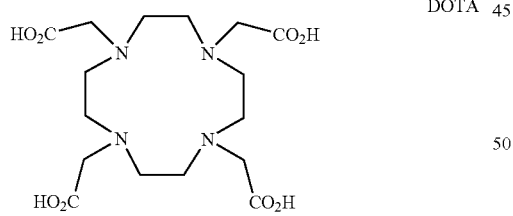

is well-known to be an effective chelator of Y(III) and lanthanides. Numerous bifunctional analogs of DOTA suitable for protein conjugation have been reported in the literature (Szilágyi et al., *Inorg. Chim. Acta.*, 2000, 298, 226–234; Kodama et al., *Inorg. Chem.*, 1991, 30, 1270–1273; Kasprzyk et al., *Inorg. Chem.*, 1982, 21, 3349–3352; Cox et al., *J. Chem. Soc. Perkin Trans.* 1, 1990, 2567–2576; Kline et al., *Bioconjugate Chem.*, 1991, 2, 26–31; and McCall et al., *Bioconjugate Chem.*, 1991, 1, 222–226). Although the Y(III)-DOTA complex shows ideal stability in vitro and in vivo, the extremely slow formation rate of the complex complicates and limits its routine use in RIT applications.

In general, DOTA conjugated to mAbs displays relatively slow and inefficient radiolabeling with Y(III) isotopes under mild conditions. This is contrary to the rapid and high-yield radiolabeling (>90%) of mAbs conjugated with bifunctional derivatives of the acyclic chelating agent diethylenetriaminepentaacetic acid (DTPA) (Stimmel et al., *Bioconjugate Chem.*, 1995, 6, 219–225; and Harrison et al., *Nucl. Med. Biol.*, 1991, 18, 469–476). Low-yield radiolabeling requires chromatographic purification of the product to separate unchelated Y(III), which is not always practical for RIT applications.

Since the release of the radiometal from the chelate is a potential source of radiotoxic effects to non-tumor cells and normal tissue, a chelate that forms a kinetically inert complex with the radiometal is critical for successful targeted radiotherapy. Complex stability comparable to that of DOTA and complexation kinetics characteristics of DTPA are also desirable. Efforts to achieve a chelate with these characteristics have resulted in the synthesis and evaluation of several chelates including CHX-DTPA:

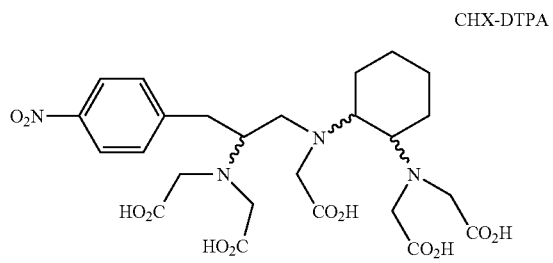

(Kobayashi et al., *J. Nucl. Med.*, 1997, 38(suppl), 824–824; McMurry et al., *J. Med. Chem.*, 1998, 41, 3546–3549; Camera et al., *J. Nuc. Med.*, 1994, 35, 882–889; Brechbiel et al, *J. Chem. Soc. Perkin Trans.* 1, 1992, 1173–1178; and Kobayashi et al., *J. Nucl. Med.*, 1998, 39, 829–836) and 1B4M-DTPA:

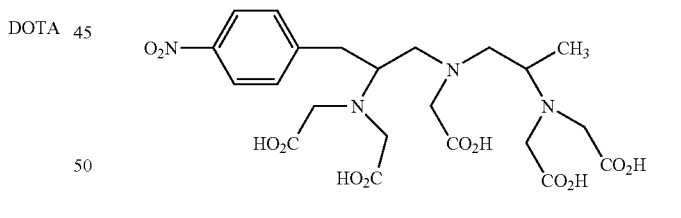

(Harrison et al., *Nucl. Med. Biol.* 1991, 18, 469–476; and Brechbiel et al., *Bioconjugate Chem.* 1991, 2, 187–194), which display significantly improved complexation kinetics with Y(III) as compared to DOTA. However, the corresponding radio-yttrium complexes remain somewhat less stable in vitro and in vivo.

Therefore, there is still a need for a compound that possesses complex stability comparable to that of DOTA, the excellent practical complexation kinetics of DTPA, and increased stability in vitro and in vivo. The invention provides such a compound. This and other objects and advantages, as well as additional inventive features, will be apparent from the description of the invention provided herein.

BRIEF SUMMARY OF THE INVENTION

The invention provides substituted 1,4,7-triazacyclononane-N,N',N''-triacetic acid compounds with a pendant donor amino group, metal complexes thereof, compositions thereof and methods of using same. The compounds of the present invention possess the same octadentate coordinating groups as DOTA and DTPA; however, these compounds have a combined macrocyclic and acyclic character. The macrocyclic component chosen is based upon 1,4,7-triazacyclononane-N,N',N''-triacetic acid ("NOTA"), while the acyclic component is a pendant bis(carboxymethyl)amino donor group that is connected by an alkylene bridge that is optionally substituted with an aralkyl group. The cooperative binding of the pendant donor groups coupled with the pre-organization and macrocyclic effect of the NOTA substructure accelerates complexation with metal ions and isotopes (e.g., Y(III), Gd(III); etc.) while maintaining a high level of stability of the complexes.

More specifically, the present invention provides a compound of the formula (Ia):

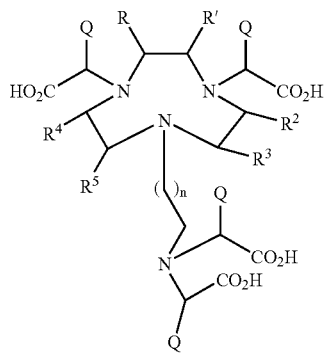

(Ia)

in which each of R, R', $R^{2-5}$ and Q are independently hydrogen, alkyl, cycloalkyl, alkoxy, hydroxyalkyl, aryl, aryloxy, hydroxyaryl, heteroaryl, thioalkyl, thioaryl, or an amino acid-containing group; and n is 1 or 2.

The present invention also provides a compound of the formula (Ib):

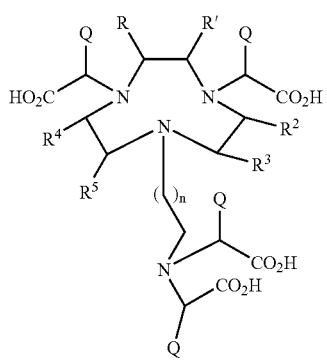

(Ib)

in which one of R, R', $R^{2-5}$ and Q is selected from the group consisting of alkyl, cycloalkyl, alkoxy, hydroxyalkyl, aryl, aryloxy, hydroxyaryl, heteroaryl, thioalkyl, thioaryl, and an amino acid-containing group and the remaining substituents (i.e., R, R', $R^2$, $R^3$, $R^4$, $R^5$, and Q) are each independently hydrogen, alkyl, cycloalkyl, alkoxy, hydroxyalkyl, aryl, aryloxy, hydroxyaryl, heteroaryl, thioalkyl, thioaryl, or an amino acid-containing group; and n is 1 or 2.

Further provided is a compound of the formula (II):

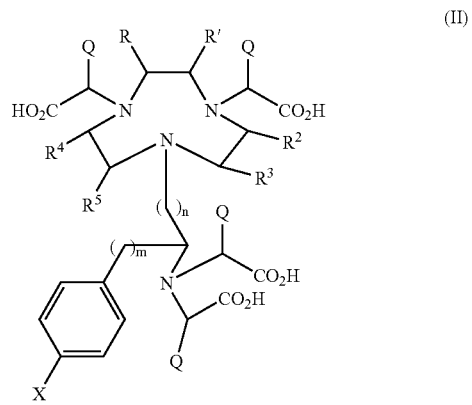

(II)

in which each of R, R', $R^{2-5}$ and Q are independently hydrogen, alkyl, cycloalkyl, alkoxy, hydroxyalkyl, aryl, aryloxy, hydroxyaryl, heteroaryl, thioalkyl, thioaryl, or an amino acid-containing group; X is hydrogen, halo, alkyl, hydroxy, nitro, amino, alkylamino, thiocyano, isothiocyano, carboxyl, carboxyalkyl, carboxyalkyloxy, amido, alkylamido, or haloalkylamido; n is 1 or 2; and m is 1–5.

Still further provided is a complex comprising the compound of Formula (Ia), (Ib) or (II) and a metal ion.

A pharmaceutical composition comprising a pharmaceutically acceptable carrier and a compound of Formula (Ia), (Ib), or (II), or a metal complex thereof is also provided.

A method for obtaining a diagnostic image of a host is further provided. The method comprises administering to the host a complex of formula (Ia), (Ib), or (II), in an amount effective to provide an image; and exposing the host to an energy source, whereupon a diagnostic image of the host is obtained.

Still further provided is a method for treating a cellular disorder in a mammal. The method comprises administering to the mammal a complex of formula (Ia), (Ib), or (II) in an amount effective to treat the cellular disorder, whereupon the cellular disorder in the mammal is treated.

DETAILED DESCRIPTION OF THE INVENTION

Figure 1:
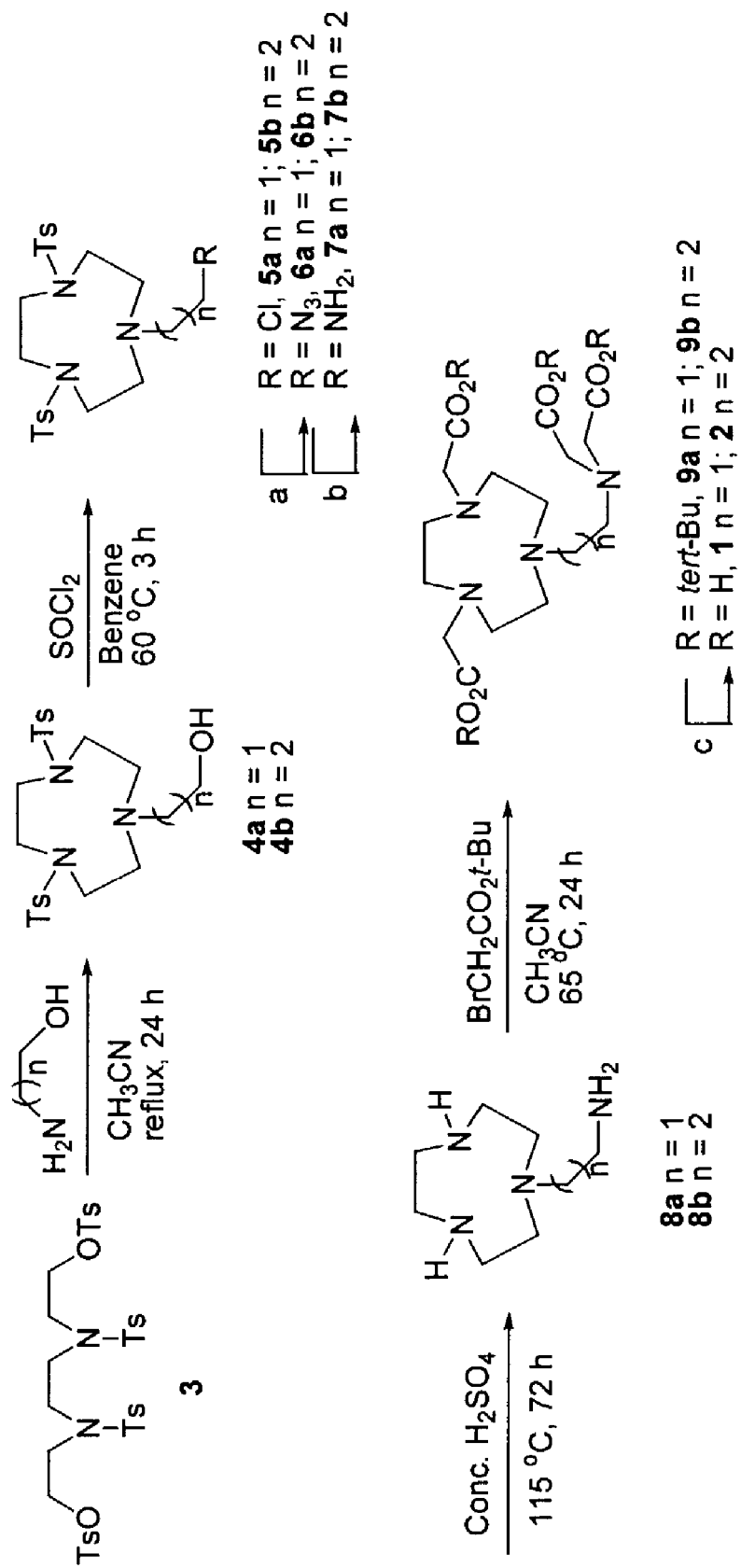
FIG. 1 illustrates the chemical synthesis of [2-(4,7-bis-carboxymethyl)-[1,4,7]triazacyclononan-1-yl-ethyl]-carbonylmethyl-amino]-acetic acid tetrahydrochloride (1) and [3-(4,7-bis-carboxymethyl)-[1,4,7]triazacyclononan-1-yl-propyl]-carbonyl-methylamino]-acetic acid tetrahydrochloride (2).

The present invention provides a compound of the formula (Ia):

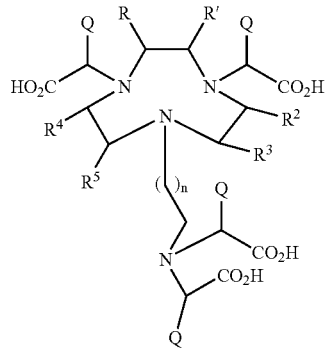

(Ia)

in which each of R, R', $R^{2-5}$ and Q are independently hydrogen, alkyl, cycloalkyl, alkoxy, hydroxyalkyl, aryl, aryloxy, hydroxyaryl, heteroaryl, thioalkyl, thioaryl, or an amino acid-containing group; and n is 1 or 2.

The present invention also provides a compound of the formula (Ib):

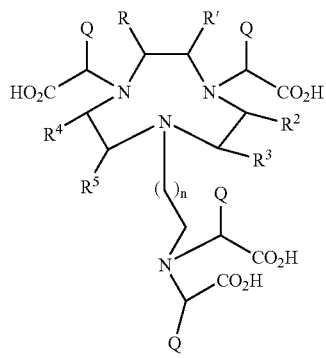

(Ib)

in which one of R, R', $R^{2-5}$ and Q is selected from the group consisting of alkyl, cycloalkyl, alkoxy, hydroxyalkyl, aryl, aryloxy, hydroxyalkyl, heteroaryl, thioalkyl, thioaryl, and an amino acid-containing group and the remaining substituents (i.e., R, R', $R^2$, $R^3$, $R^4$, $R^5$, and Q) are each independently hydrogen, alkyl, cycloalkyl, alkoxy, hydroxyalkyl, aryl, aryloxy, hydroxyaryl, heteroaryl, thioalkyl, thioaryl, or an amino acid-containing group; and n is 1 or 2.

A preferred compound of formula (Ia) or (Ib) is one in which R and R' are methyl. More preferably, R and R' are methyl groups that are trans to one another. More preferably, R and R' together form a cycloalkyl group. For example, R and R' together form a 1,2-cyclohexyl ring; desirably the ring is in the trans geometry.

The invention also provides a compound of the formula (II):

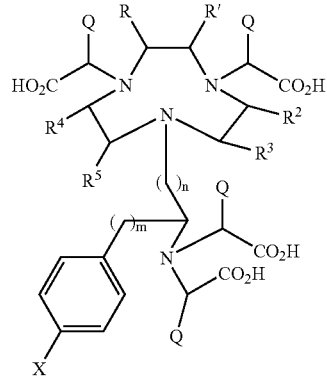

(II)

in which each of R, R', $R^{2-5}$ and Q are independently hydrogen, alkyl, cycloalkyl, alkoxy, hydroxyalkyl, aryl, aryloxy, hydroxyaryl, heteroaryl, thioalkyl, thioaryl, or an amino acid-containing group; X is hydrogen, halo, alkyl, hydroxy, nitro, amino, alkylamino, thiocyano, isothiocyano, carboxyl, carboxyalkyl, carboxyalkyloxy, amido, alkylamido, or haloalkylamido; n is 1 or 2; and m is 1–5. Preferably, m is 1 to 3, more preferably m is 1 to 2, and most preferably, m is 2. It is most desirable for m to be 2 because the aralkyl group is spaced sufficiently far enough from the chelating NOTA compound. Compounds in which m is greater than 3 involve a more complicated synthetic route.

A preferred compound of formula (II) is one in which R and R' are methyl. More preferably, R and R' together form a cycloalkyl group. For example, R and R' together form a 1,2-cyclohexyl ring; desirably the ring is in the trans geometry.

Any of the groups indicated above for R, R', $R^{2-5}$, Q and X can optionally be substituted with 1 to 6 (e.g., 1 to 4, 1 to 3) substituents. Suitable substituents include hydroxy, $C_{1-12}$ alkoxy, acyloxy, halo, benzyl, acetyl, carboxyl, carboxy-$C_{1-12}$ alkyl, such as carboxymethyl, carboxyethyl, carboxy-$C_{1-12}$ alkylamido, carboxy-$C_{1-12}$ dialkylamido, carboxamido, amino, $C_{1-12}$ alkylamino, $C_{1-12}$ dialkylamino, $C_{1-12}$ alkylcarbonyl, $C_{6-30}$ arylamino, $C_{6-30}$ diarylamino, cyano, tolyl, xylyl, mesityl, anisyl, pyrrolidinyl, formyl, thio, $C_{1-12}$ alkylthio, $C_{6-30}$ aryl, $C_{5-30}$ heteroaryl, such as pyranyl, pyrrolyl, furanyl, thiophenyl, thiazolyl, pyrazolyl, pyridinyl, or pyrimidinyl, phenoxy, benzyloxy, phenylcarbonyl, benzylcarbonyl, nitrophenyl $C_{1-12}$ trialkylsilyl, nitro, sulfonyl, nitrobenzyl, $C_{1-12}$ trialkylammonium, $C_{1-12}$ alkyl, $C_{3-8}$ cycloalkyl, tetrahydrofuranyl, tetrahydropyranyl, piperidinyl and morpholinyl.

Referring now to terminology used generically herein, the term "alkyl" means a straight-chain or branched alkyl substituent containing from, for example, about 1 to about 12 carbon atoms, preferably from about 1 to about 8 carbon atoms, more preferably from about 1 to about 6 carbon atoms. Examples of such substituents include methyl, ethyl, propyl, isopropyl, n-butyl, sec-butyl, isobutyl, tert-butyl, pentyl, isoamyl, hexyl, octyl, dodecanyl, and the like.

The term "cycloalkyl," as used herein, means a cyclic alkyl substituent containing from, for example, about 3 to about 30 carbon atoms, preferably from about 5 to about 14 carbon atoms, more preferably from about 5 to about 10 carbon atoms, and most preferably from about 5 to about 7 carbon atoms. Examples of such substituents include cyclopropyl, cyclobutyl, cyclopentyl, cyclohexyl, and the like.

The term "halo" or "halogen," as used herein, means a substituent selected from Group VIIA, such as, for example, fluorine, bromine, chlorine, and iodine. Preferably, the halo is bromine or iodine.

The term "aryl" refers to an unsubstituted or substituted aromatic carbocyclic substituent, as commonly understood in the art, and includes monocyclic and polycyclic aromatics such as, for example, phenyl, biphenyl, toluenyl, anisolyl, naphthyl, anthracenyl and the like. An aryl substituent generally contains from, for example, about 3 to about 30 carbon atoms, preferably from about 6 to about 18 carbon atoms, more preferably from about 6 to about 14 carbon atoms and most preferably from about 6 to about 10 carbon atoms. It is understood that the term aryl applies to cyclic substituents that are planar and comprise $4n+2$ $\pi$ electrons, according to Hückel's Rule.

The term "heteroaryl" means a substituent defined by an aromatic heterocyclic ring, as is commonly understood in the art, including monocyclic and polycyclic heteroaryls containing from, for example, about 3 to about 30 carbon atoms, preferably from about 5 to about 10 carbon atoms, more preferably from about 5 to about 6 carbon atoms. Monocyclic heteroaryls include, for example, imidazolyl, thiazolyl, pyrazolyl, pyrrolyl, furanyl, pyrazolinyl, thiophenyl, oxazolyl, isoxazolyl, pyridinyl, pyridonyl, pyrimidinyl, pyrazinyl, and triazinyl substituents. Polycyclic heteroaryls include, for example, quinolinyl, isoquinolinyl, indolyl, purinyl, benzimidazolyl, benzopyrrolyl, and benzothiazolyl.

The term "alkoxy" embraces linear or branched alkyl groups that are attached to divalent oxygen. The alkyl group is the same as described herein. Examples of such substituents include methoxy, ethoxy, t-butoxy, and the like. The aryl group is the same as described herein. The term "aryloxy" refers to substituents that have an aryl group attached to divalent oxygen. Examples of such substituents include phenoxy.

The term "alkylthio" as used herein, denotes a substituent with an alkyl group directly attached to a divalent sulfur atom. The alkyl group is the same as described herein. Examples of such substituents include methylthio, ethylthio, and the like. Similarly, the term "arylthio" as used herein, denotes a substituent with an aryl group directly attached to a divalent sulfur atom. The aryl group is the same as described herein.

The term "carboxyl" refers to the group —C(O)OH. The term "carboxyalkyl" refers to the group —RC(O)OH that is connected to the compound through the alkyl R group. The term "carboxyalkyloxy" refers to the group —ORC(O)OH, in which the R is an alkyl (e.g., $(CH_2)_n$ alkylene group, n is 1 to 12) group.

The term "alkylamino" refers to a secondary amine substituent with one hydrogen and one alkyl group directly attached to a trivalent nitrogen atom. In addition, the term "alkylamino" also refers to a tertiary amine substituent with two of the same or different alkyl groups directly attached to a trivalent nitrogen atom. The alkyl group is the same as described herein.

The term "alkylamido" refers to substituents of the formula, —C(O)NRR' or —NRC(O)R', in which R and R' are the same or different and each is a hydrogen or alkyl group, as described herein. The term "haloalkylamido" is an alkylamido as described above, in which one or more of the alkyl groups is substituted with a halo moiety, such as, for example, chlorine, bromine or iodine.

The term "amino acid-containing group" refers to substituents that include both a carboxyl group (C(O)OH) and an amino group ($NH_2$). Commonly, such substituents have the generic formula, —RCH($NH_2$)$CO_2$H, in which the substituent bonds to a compound of Formula (Ia), (Ib) or (II) through the R group. While any amino acid is to be considered (e.g., glycinyl, alaninyl, leucinyl, etc.) acceptable as a substituent, asparate (—CH($NH_2$)$CO_2$H) and glutamate (—$CH_2$CH($NH_2$)$CO_2$H) are especially preferred. Therefore, when Q of formula (Ia), (Ib) or (II) is asparate or glutamate, the entire nitrogen substituent forms aspartic acid or glutamic acid, respectively.

For the preparation of compounds of formula (Ia), (Ib) or (II), efficient cyclization using two precursor molecules is a crucial step. A variety of cyclization methods in synthesis of macrocyclic chelating agents have been developed (see, for example, McMurry et al., *Bioconjugate Chem.*, 1992, 3, 108–117; Curtis et al., *J. Chem. Soc. A*, 1966, 1015–1018; Renn et al., *Bioconjugate Chem.*, 1992, 3, 563–569; Cox et al., *J. Chem. Soc., Perkin Trans.* 1, 1990, 2567–2576; Kovacs et al., *Synth. Commun.*, 1999, 29, 2817–2822; and Weisman et al., *J. Org. Chem.*, 1995, 61, 5186–5187). Representative synthetic methods for bi-molecular cyclization include reaction of a diamine and diester under high dilution conditions (McMurry et al., supra), metal-templated cyclization (Curtis et al., supra), and the Richman-Atkin's cyclization conditions (Cox et al., supra). These cyclization methods, when employed to prepare smaller polyaza macrocyclic stuctures, are frequently problematic, resulting in low yields, inconvenient procedures, and difficult purification regimens due to the presence of higher homolog by-products.

While any method can be used to prepare compounds of formula (Ia), (Ib) or (II), the synthetic methods provided herein are preferred. The methods offer a convenient approach to cyclization by employing primary amines with a pendant hydroxyl functional group as a precursor molecule. In general, primary amines bearing a distal hydroxyl group are reacted with an N-tosyl protected ditosylate to provide a 1,4,7-triazacyclononane macrocyclic ring. After cyclization, the pendant hydroxyl group is available for further chemistry to introduce additional pendant donor groups as desired. This cyclization method is a convenient, clean, and high-yield route using readily available starting materials. This strategy can be directly applied to construct a wide range of macrocyclic rings by using functionalized primary amines (e.g., alkyl substituted, aryl substituted, etc.). In brief, the requisite substituted diamines and subsequent substituted diethanolamines are readily available from extensive literature and the host of possibilities associated with amino acids to provide not only desired substituents and the appropriate regiochemistry, but also to provide them in desirable stereochemistry. This is equally the case for the other cyclization component. Additionally, the stereoselective introduction of substituents on the carboxylate functional groups is also readily available from routine, well-established amino acid chemistry.

The functionality of the substituents (i.e., R, R', $R^2$, $R^3$, $R^4$, $R^5$, Q and X) of the compounds of the invention allow derivatization to biomolecules. The term "biomolecule" refers to all natural and synthetic molecules that play a role in biological systems. Biomolecules include hormones, amino acids, peptides, peptidomimetics, proteins, deoxyribonucleic acid (DNA), ribonucleic acid (RNA), lipids, albumins, polyclonal antibodies, receptor molecules, receptor binding molecules, haptens, monoclonal antibodies and aptamers. Specific examples of biomolecules include insulins, prostaglandins, growth factors, liposomes and nucleic acid probes. An advantage of using biomolecules is tissue targeting through specificity of delivery.

Any suitable hapten can be linked with a compound of formula (Ia), (Ib) or (II). Haptens such as hormones, steroids, enzymes and proteins are desirable in some applications because of their site specificity to tumors and/or various organs of the body. A preferred hapten for use in treating cellular disorders or various disease conditions is a monoclonal antibody. Methods of bonding a macrocyclic compound to a hapten are described in U.S. Pat. No. 5,428,154, which are incorporated herein by reference.

Coupling of a compound of formula (Ia), (Ib) or (II) to one or more biomolecules can be accomplished by several known methods (see, for example, Krejcarek et al., *Biochem. Biophys. Res. Commun.*, 1977, 30, 581; Hnatowich et al., *Science*, 1983, 220, 613). For example, a reactive moiety present in one of the substituents (i.e., R, R', $R^{2-5}$, Q or X) is coupled with a second reactive group located on the biomolecule. Typically, a nucleophilic group is reacted with an electrophilic group to form a covalent bond between the biomolecule and the compound of formula (Ia), (Ib) or (II). Examples of nucleophilic groups include amines, anilines, alcohols, phenols, thiols and hydrazines. Examples of electrophilic groups include halides, disulfides, epoxides, maleimides, acid chlorides, anhydrides, mixed anhydrides, activated esters, imidates, isocyanates and isothiocyanates.

Preferably, a compound of formula (II) is bonded to a biomolecule through the X substituent. It is especially preferred that the X substituent of formula (II) is a substituent that conjugates the compound to a hapten. This substituent is desirably a free-end nitro group, which can be reduced to an amine. The amine then can be activated with a compound, such as thionyl chloride, to form a reactive chemical group, such as an isothiocyanate. An isothiocyanate is preferred because it links directly to an amino residue of a hapten, such as an mAb. The aniline group can be linked to an oxidized carbohydrate on the protein and, subsequently, the linkage fixed by reduction with cyanoborohydride. The amino group also can be reacted with bromoacetyl chloride or iodoacetyl chloride to form —$NHCOCH_2Z$, with Z being bromide or iodide. This group reacts with any available amine or sulfhydryl group on a hapten to form a stable covalent bond. If tyrosine is used in the formulation of the macromolecule, a carboxylic acid or methoxy carboxylate group can be in this position of the compound. The most desirable X substituents for compounds of formula (II) are members selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido. In some preferred instances, X is a haloalkylamido of the formula —$NHCOCH_2Z$, with Z being bromide or iodide. Another preferred substituent for this position is isothiocyano (—NCS).

The invention also relates to a complex comprising the compound of formula (I), (II) or (III) and a metal ion, in which is the metal ion is optionally radioactive. The metal ion is any metal ion that is suitable for the desired end use of the complex. For example, in proton magnetic resonance imaging, paramagnetic metal atoms such as gadolinium(III), manganese(II), manganese(III), chromium(III), iron(II), iron(III), cobalt(II), nickel(II), copper(II), praseodymium(III), neodymium(III), samarium(III), ytterbium(III), terbium(III), dysprosium(III), holmium(III), and erbium(III) (all are paramagnetic metal atoms with favorable electronic properties) are preferred as metals complexed by the ligands of formula (I), (II) or (III). Gadolinium(III) is the most preferred complexed metal due to the fact that it has the highest paramagnetism, low toxicity when complexed to a suitable ligand, and high lability of coordinated water. Typical metal ions for forming a complex of the invention include Ac, Bi, Pb, Y, Mn, Cr, Fe, Co, Ni, Tc, In, Ga, Cu, Re, a lanthanide (i.e., any element with atomic number 57 to 71 inclusive) and an actinide (i.e., any element with atomic number 89 to 103 inclusive). For use as x-ray contrast agents, the metal ion must be able to absorb adequate amounts of x-rays (i.e., radio-opaque), such as, for example, indium, yttrium, lead, bismuth, gadolinium, dysprosium, holmium and praseodymium.

Compounds of formula (I), (II) or (III) also can be complexed with a radioactive metal ion for use as therapeutic agents (e.g., radiopharmaceuticals). Radioisotopes of any suitable metal ion are acceptable for forming metal complexes of the invention. For example, typical radioisotopes include technetium, bismuth, lead, actinium, carbon, nitrogen, iodine, fluorine, oxygen, tellurium, helium, indium, gallium, copper, rhenium, yttrium, samarium, zirconium, lutetium and holmium. Of these radioisotopes, yttrium is preferred. Specific examples of radionuclides suitable for complexing to a compound of formula (I), (II) or (III) for various imaging techniques, including single photon emission computed spectroscopy, are, for example, $^{213}Bi$, $^{212}Bi$, $^{212}Pb$, $^{225}Ac$, $^{177}Lu$, $^{111}In$, $^{166}Ho$, $^{90}Y$, $^{153}Sm$, $^{67}Cu$, $^{64}Cu$, $^{66}Ga$, $^{68}Ga$, $^{86}Y$, $^{89}Zr$ and $^{67}Ga$.

To prepare metal complexes of the invention, compounds of formula (Ia), (Ib) or (II) are complexed with an appropriate metal or metal ion. This can be accomplished by any methodology known in the art. For example, the metal can be added to water in the form of an oxide, halide, nitrate or acetate (e.g., yttrium acetate, bismuth iodide) and treated with an equimolar amount of a compound of formula (Ia), (Ib) or (II). The compound can be added as an aqueous solution or suspension. Dilute acid or base can be added (where appropriate) to maintain a suitable pH. Heating at temperatures as high as 100° C. for periods of up to 24 hours or more can be employed to facilitate complexation, depending on the metal, the compound, and their concentrations.

Pharmaceutically acceptable salts of the metal complexes of the compounds of formula (Ia), (Ib) or (II) are also useful as imaging agents. These salts can be prepared by using a base (e.g., an alkali metal hydroxide, meglumine, arginine or lysine) to neutralize the above-prepared metal complexes, while they are still in solution. Some of the metal complexes are formally uncharged and do not need cations as counterions. Such neutral complexes may be preferred as intravenously administered x-ray and NMR imaging agents over charged complexes because they may provide solutions of greater physiologic tolerance due to their lower osmolality. However, for use as hepatobiliary agents, negatively charged ligands are preferred.

The invention provides a pharmaceutical composition comprising a pharmaceutically acceptable carrier and a compound of formula (Ia), (Ib), (II), or a metal complex thereof. Preferably, the pharmaceutical composition further comprises a pharmaceutically acceptable carrier. The pharmaceutically acceptable carriers described herein, for example, vehicles, adjuvants, excipients, and diluents, are well-known to those skilled in the art and are readily available to the public. The choice of carrier will be determined, in part, by the particular composition and by the particular method used to administer the composition. Accordingly, there are a wide variety of suitable formulations of the pharmaceutical compositions of the present invention.

One skilled in the art will appreciate that suitable methods of administering a composition of the present invention to an animal, e.g., a mammal such as a human, are also known. Although more than one route can be used to administer a particular composition, a particular route can provide a more immediate and more effective result than another route.

Formulations suitable for oral administration can consist of (a) liquid solutions, such as an effective amount of the compound of formula (Ia), (Ib) or (II) dissolved in a diluent, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The compounds of formula (Ia), (Ib) or (II), alone or in combination with other suitable components, can be made into aerosol formulations to be administered via inhalation. These aerosol formulations can be placed into pressurized acceptable propellants, such as dichlorodifluoromethane, hydrofluorocarbon (such as HFC 134a and/or 227), propane, nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame or an amount sufficient to allow for diagnostic imaging of the desired tissue or organ. The dose will be determined by the strength of the particular compositions employed and the condition of the animal (e.g., human), as well as the body weight of the animal (e.g., human) to be treated. The size of the dose also will be determined by the existence, nature, and extent of any adverse side effects that might accompany the administration of a particular composition. A suitable dosage for internal administration is 0.01 to 100 mg/kg of body weight per day, such as 0.01 to 35 mg/kg of body weight per day or 0.05 to 5 mg/kg of body weight per day. A suitable concentration of the compound in pharmaceutical compositions for topical administration is 0.05 to 15% (by weight), preferably 0.02 to 5%, and more preferably 0.1 to 3%.

A method for obtaining a diagnostic image of a host is provided by the present invention. In particular, the method comprises administering to the host a complex of formula (Ia), (Ib), or (II), in an amount effective to provide an image; and exposing the host to an energy source, whereupon a diagnostic image of the host is obtained. The diagnostic image can be, for example, a magnetic resonance image, an x-ray contrast image, single photon emission computed spectroscopy (SPECT) image or the like.

For example, the compounds of formula (Ia), (Ib) or (II), can be complexed with a paramagnetic metal atom and used as relaxation enhancement agents for magnetic resonance imaging. These agents, when administered to a host (e.g., a mammal such as a human) distribute in various concentrations to different tissues, and catalyze the relaxation of protons in the tissues that have been excited by the absorption of radiofrequency energy from a magnetic resonance imager. This acceleration of the rate of relaxation of the excited protons provides for an image of different contrast when the host is scanned with a magnetic resonance imager. The magnetic resonance imager is used to record images at various times, generally either before and after administration of the agents, or after administration only, and the differences in the images created by the presence of the agent in tissues are used in diagnosis. Guidelines for performing imaging techniques can be found in Stark et al., *Magnetic Resonance Imaging,* Mosbey Year Book: St. Louis, 1992, hereby incorporated by reference.

Accordingly, the present invention provides a method for magnetic resonance imaging of a host (e.g., mammal, such as a human). The method comprises administering to the host a complex of any of formula (Ia), (Ib) or (II), in which the metal is paramagnetic, in an amount effective to provide an image; and exposing the host to a magnet, whereupon a magnetic resonance image of the host is obtained. Preferably a complex used in obtaining a magnetic resonance image comprises Gd. Paramagnetic metal complexes of the present invention are particularly useful as hepatobiliary agents, i.e., for magnetic resonance imaging of the liver and bile ducts.

While the above-described uses for the metal-chelating ligands of the present invention are preferred, those working in the diagnostic arts will appreciate that the ligands also can be complexed with the appropriate metals and used as contrast agents in other imaging techniques, such as x-ray imaging, radionuclide imaging and ultrasound imaging, and in radiotherapy. Accordingly, the present invention further provides a method for x-ray imaging of a host. The method comprises administering to the host a complex of any of formula (Ia), (Ib) or (II), in which the metal ion is radio-opaque, in an amount effective to provide an image; and exposing the host to x-rays, whereupon an x-ray contrast image of the host is obtained. The usefulness of metal ions in in vitro and in vivo diagnostic procedures is disclosed in U.S. Pat. No. 4,454,106, hereby incorporated by reference. X-ray contrast imaging procedures can be found in Moss et al., *Computed Tomography of the Body,* W. D. Saunders Company: Philadelphia, 1992; and M. Sovak, Editor, *Radiocontrast Agents,* Springer-Verlag: Berlin, 1984, hereby incorporated by reference.

The most desirable embodiment of this diagnostic process uses $^{111}$In. The radioactive probe $^{111}$In decays with a half life of 2.8 days (67 hours) to an excited state of the daughter nucleus $^{111}$Cd. From this excited state, a cascade of two gamma-rays is emitted, encompassing an isomeric state with a half life of 85 ns. $^{111}$In is useful for single photon emission computed spectroscopy (SPECT), which is a diagnostic tool. Thus, when $^{111}$In is complexed to a compound of Formula (Ia), (Ib) or (II) and linked to a biomolecule, such as a hapten, which specifically localizes in a tumor, then that particular localization can be three-dimensionally mapped for diagnostic purposes in vivo by single photon emission tomography. Alternatively, the emission can be used in vitro in radioimmunoassays. The present invention provides a method for SPECT imaging of a host (e.g., mammal, such as a human). The method comprises administering to the host a complex of any of formula (Ia), (Ib) or (II), in which the metal emits a single photon, in an amount effective to provide an image; and exposing the host to an energy source, whereupon a SPECT image of the host is obtained.

Also provided is a method for treating a cellular disorder in a mammal. The method comprises administering to the mammal (e.g., human) a complex of the present invention in an amount effective to treat the cellular disorder, whereupon the cellular disorder is treated. A preferred complex comprises Pb or Y, in particular $^{90}$Y. The treatment can be prophylactic or therapeutic. By "prophylactic" is meant any degree in inhibition of the onset of the cellular disorder, including complete inhibition. By "therapeutic" is meant any degree in inhibition or any degree of beneficial effects on the disorder in the mammal (e.g., human), e.g., inhibition of the growth or metastasis of a tumor.

Preferably, the method includes administration of a metal complex bound to a hapten having a selective binding site on a cell affected by the disorder. For example, Q can be bound to an mAb, wherein the antibody is directed and created against an epitope found specifically on tumor cells. Thus, when $^{212}$Pb is transported to the antigen site, and subsequently decays in secular equilibrium to $^{212}$Bi and its daughters, a beta irradiation is produced from the lead disintegration. In addition, a beta radiation is produced by the bismuth daughters. This beta radiation is similar to the beta radiation from $^{90}$Y but, in addition, each disintegration of bismuth also produces an alpha particle. In this manner, a radiotherapy is provided with a radiation dose from an alpha particle and a beta particle. If desired, only $^{212}$Bi can be introduced in those cases where the disorder to be treated, such as with leukemic cells, can be easily reached within the 1 hour half-life of $^{212}$Bi. Suitable procedures using radiopharmaceuticals can be found in the literature (see, for example, Mettler Jr. et al., *Essentials of Nuclear Medicine Imaging*, Grune and Stratton, Inc.: New York, 1983).

It is possible to use this method to treat cancer, where the cells are widely differentiated. Cancers suitable for treatment with compounds, complexes, and compositions of the invention include, for example, lymphomas, leukemias, colo-rectal cancer, ovarian cancer, breast cancer, and prostate cancer. This method might even be preferred where only a long-range beta emitter, such as $^{90}$Y, is desired. In differing environments in vivo, the $Bi^{212}$ is retained inside the chelate after the beta emission in varying amounts. Most desirably, at least 95% of $Bi^{212}$ remains in the metal complex. In an acidic medium, such as the stomach, at least about 70% of the $Bi^{212}$ is retained. Retaining at least about 80% or 90%, $Bi^{212}$ is also desirable depending on the medium.

The following examples further illustrate the invention but, of course, should not be construed as in any way limiting its scope.

EXAMPLES

All solvents and reagents were obtained from Aldrich (Milwaukee, Wis.) and used as received unless otherwise noted. $^1$H, $^{13}$C, and attached proton test (APT) NMR spectra were obtained using a Varian Gemini 300 instrument and chemical shifts are reported in ppm on the δ scale relative to tetramethylsilane (TMS), 3,3,3-trimethylsilylpropionate (TSP), or solvent. Proton chemical shifts are annotated as follows: ppm (multiplicity, integral, coupling constant (Hz)). Elemental microanalyses were performed by Galbraith Laboratories, Knoxville, Tenn. Fast atom bombardment mass spectra (FAB-MS) were obtained on an Extrel 4000 in the positive ion detection mode. Size exclusion high performance liquid chromatograms (SE-HPLC) were obtained on a Dionex isocratic system with a Waters 717 autosampler, a Gilson 112 UV detector and an in-line INIUS γ-Ram Model 2 radiodetector. Time scan measurements were obtained using HP-8452A diode array spectrophotometer. The $^{88}$Y was obtained from Los Alamos National Laboratory and purified as previously reported (Camera et al., *J. Nuc. Med.*, 1994, 35, 882–889). Phosphate buffered saline (PBS), 0.1 M of pH 7.4, consisted of 0.08 M $Na_2HPO_4$, 0.02 M $KH_2PO_4$, 0.01 M KCl, and 0.14 M NaCl.

Appropriate shielding and handling protocols were utilized when using $^{88}$Y ($t_{1/2}$=106.6 day), as it is a γ-emitting radionuclide.

Example 1

This example describes a general procedure for synthesis of macrocyclics 4a and 4b (FIG. 1).

To a solution of 3 (1 mmol); (Nicolas et al., *J. Labelled Comp. Radiopharm.*, 2000, 43, 585–594) and $Na_2CO_3$ (10 mmol) in $CH_3CN$ (10 mL) under argon was added either ethanolamine or propanolamine (1 mmol), and the resulting mixture was heated to reflux for 24 h. The reaction mixture was allowed to cool gradually to ambient temperature, filtered, and the filtrate was concentrated in vacuo.

Example 2

This example describes the purification of 2-[-4,7-bis-(p-toluene-4-sulfonyl)-[1,4,7]triazacyclononan-1-yl]-ethanol (4a) (FIG. 1).

The residue from Example 1 was purified via column chromatography on silica gel eluting with ethyl acetate (EtOAc). Pure 4a (414 mg, 86%) was thereby obtained as a colorless oil: $^1$H NMR (CDCl$_3$) δ 2.03 (s, 1 H), 2.40 (s, 6 H), 2,79 (t, $J_{AB}$=3.2 Hz, 2 H), 3.01 (t, $J_{AB}$=3.8 Hz, 4 H), 3.26 (t, $J_{AB}$=3.6 Hz, 4 H), 3.44 (t, $J_{AB}$=1.8 Hz, 4 H), 3.61 (t, $J_{AB}$=2.7 Hz, 2 H), 7.31 (AB, $J_{AB}$=9.1 Hz, 4 H), 7.67 (AB, $J_{AB}$=9.1 Hz, 4 H); $^{13}$C NMR (CDCl$_3$) δ 21.2 (q), 52.3 (t), 52.7 (t), 54.9 (t), 59.3 (t), 59.9 (t), 126.8 (d), 129.5 (d), 134.8 (s), 143.2 (s). Anal. Calcd for $C_{22}H_{31}N_3S_2O_5$: C, 54.86; H, 6.49. Found: C, 54.51; H, 6.64.

Example 3

This example describes the purification of 3-[-4,7-bis-(p-toluene-4-sulfonyl)-[1,4,7]triazacyclononan-1-yl]-propan-1-ol (4b) (FIG. 1).

The residue from Example 1 was purified via column chromatography on silica gel eluting with EtOAc. Pure 4b (454 mg, 92%) was thereby obtained as a colorless oil: $^1$H NMR (CDCl$_3$) δ 1.78 (t, $J_{AB}$=3.5 Hz, 2 H), 2.13 (s, 1 H), 2.50 (s, 6 H), 2.87 (t, $J_{AB}$=3.3 Hz, 2 H), 3.04–3.12 (m, 4 H), 3.26–3.41 (m, 4 H), 3.50 (s, 2 H), 3.87 (t, $J_{AB}$=2.9 Hz, 4 H), 7.40 (AB, $J_{AB}$=8.7 Hz, 4 H), 7.41 (AB, $J_{AB}$=8.7 Hz, 4 H); $^{13}$C NMR (CDCl$_3$) δ 21.4 (q), 29.5 (t), 51.5 (t), 52.8 (t), 54.4 (t), 54.7 (t), 61.5 (t), 127.0 (d), 129.7 (d), 135.0 (s), 143.5 (s). Anal. Calcd for $C_{23}H_{33}N_3S_2O_5$: C, 55.74; H, 6.71. Found: C, 55.87; H, 6.84.

Example 4

This example describes a general procedure for chlorination of 5a and 5b (FIG. 1).

A solution of either 4a or 4b (2 mmol) in dry benzene (20 mL) was saturated with HCl(g) at 0° C. After addition of thionyl chloride (40 mmol), the mixture was heated at 60° C. for 3 h. The cooled reaction mixture was concentrated and neutralized with 5% $Na_2CO_3$ solution (5 mL). The resulting mixture was extracted with $CH_2Cl_2$ (3×50 mL), the combined organic layers were dried ($MgSO_4$) and filtered, and the filtrate was concentrated in vacuo.

Example 5

This example describes the purification of 1-(2-chloroethyl)-bis-(p-toluene-4-sulfonyl)-[1,4,7]triazacyclononane (5a) (FIG. 1).

The residue from Example 4 was purified via column chromatography on silica gel eluting with 20% EtOAc-hexane. Pure 5a was obtained as a colorless oil (930 mg, 93%): $^1$H NMR (CDCl$_3$) δ 2.53 (s, 6 H), 3.05–3.14 (m, 8 H), 3.62–3.75 (m, 8 H), 7.42 (AB, $J_{AB}$=9.2 Hz, 4 H), 7.67 (AB, $J_{AB}$=9.2 Hz, 4 H); $^{13}$C NMR (CDCl$_3$) δ 21.4 (q), 42.4 (t), 51.4 (t), 52.6 (t), 56.3 (t), 59.0 (t), 127.1 (d), 129.7 (d), 135.2 (s), 143.8 (s). Anal. Calcd for $C_{22}H_{30}N_3S_2O_4Cl$: C, 52.84; H, 6.05. Found: C, 52.78; H, 6.35.

Example 6

This example describes the purification of 1-(3-chloropropyl)-bis-(p-toluene-4sulfonyl)-[1,4,7]triazacyclononane (5b) (FIG. 1).

The residue from Example 4 was purified via column chromatography on silica gel eluting with 15% EtOAc-hexane. Pure 5b was obtained as a colorless oil (966 mg, 94%): $^1$H NMR (CDCl$_3$) δ 2.00 (t, $J_{AB}$=6.1 Hz, 2 H), 2.51 (s, 6 H), 2.82 (t, $J_{AB}$=6.0 Hz, 2 H), 2.94–2.94 (m, 4 H), 3.33 (s, 4 H), 3.58 (s, 2 H), 3.80 (t, $J_{AB}$=6.0 Hz, 4 H), 7.41 (AB, $J_{AB}$=8.7 Hz, 4 H), 7.75 (AB, $J_{AB}$=8.7 Hz, 4 H); $^{13}$C NMR (CDCl$_3$) δ 21.3 (q), 30.1 (t), 43.1 (t), 51.4 (t), 52.7 (t), 53.5 (t), 55.7 (t), 127.0 (d), 129.7 (d), 135.0 (s), 143.4 (s). HRMS (positive ion FAB) Calcd for $C_{23}H_{32}N_3S_2O_4Cl$: [M+H]$^+$ m/z 514.1601. Found: [M+H]$^+$ m/z 514.1600. Anal. Calcd for $C_{23}H_{32}N_3S_2O_4Cl(H_2O)_{0.5}$: C, 52.81; H, 6.36. Found: C, 52.72; H, 6.49.

Example 7

This example describes a general procedure for the reaction of 5a and 5b with azide (FIG. 1).

A mixture of compound 5a or 5b (3.3 mmol) and $NaN_3$ (6.93 mmol) in DMSO (20 mL) was heated to 90° C. for 4 h. The resulting mixture was poured into ice water and extracted with ethyl ether (2×50 mL). The combined organic layers were washed with $H_2O$ (3×50 mL), dried ($MgSO_4$), filtered, and concentrated in vacuo.

Example 8

This example describes the purification of 1-(2-azidoethyl)-4,7-bis-(p-toluene-4-sulfonyl)-[1,4,7]triazacyclononane (6a) (FIG. 1).

The crude 6a from Example 7 can be used directly for the next step or purified via column chromatography on neutral alumina eluting with 15% $CH_2Cl_2$-hexane. Pure 6a (1.56 g, 96%) was thereby obtained as a colorless viscous oil: $^1$H NMR (CDCl$_3$) δ 2.44 (s, 6 H), 2.82 (t, $J_{AB}$=6.2 Hz, 4 H), 2.99 (s, 2 H), 3.18–3.35 (m, 4 H), 3.38 (t, $J_{AB}$=6.2 Hz, 4 H), 3.54 (s, 2 H), 7.34 (AB, $J_{AB}$=8.7 Hz, 4 H), 7.71 (AB, $J_{AB}$=8.7 Hz, 4 H); $^{13}$C NMR (CDCl$_3$) δ 21.4 (q), 49.5 (t), 51.0 (t), 52.1 (t), 55.4 (t), 55.5 (t), 126.7 (d), 129.4 (d), 134.9 (s), 143.1 (s). Anal. Calcd for $C_{22}H_{30}N_6S_2O_4$: C, 52.16; H, 5.97. Found: C, 52.33; H, 6.10.

Example 9

This example describes the purification of 1-(3-azidopropyl)-4,7-bis-(p-toluene-4-sulfonyl)-[1,4,7]triazacyclononane (6b) (FIG. 1).

The crude 6b from Example 7 can be used directly for the next step or purified via column chromatography on neutral alumina eluting with 15% $CH_2Cl_2$-hexane. Pure 6b (1.54 g, 92%) was thereby obtained as a colorless viscous oil: $^1$H NMR (CDCl$_3$) δ 1.84 (t, $J_{AB}$=5.1 Hz, 2 H), 2.52 (s, 6 H), 2.75 (t, $J_{AB}$=6.8 Hz, 2 H), 2.90–3.04 (m, 4 H), 3.30 (s, 4 H), 3.49–3.64 (s, 6 H), 7.41 (AB, $J_{AB}$=8.6 Hz, 4 H), 7.53 (AB, $J_{AB}$=8.6 Hz, 4 H); $^{13}$C NMR (CDCl$_3$) δ 21.4 (q), 27.0 (t), 49.1 (t), 51.5 (t), 52.7 (t), 53.8 (t), 55.5 (t), 127.1 (d), 129.7 (d), 135.0 (s), 143.5 (s). HRMS (positive ion FAB) Calcd for $C_{23}H_{32}N_6S_2O_4$: [M+H]$^+$ m/z 521.2005. Found: [M+H]$^+$ m/z 521.1996. Anal. Calcd for $C_{23}H_{32}N_6S_2O_4(H_2O)_{0.5}$: C, 52.16; H, 6.28. Found: C, 52.02; H, 6.26.

Example 10

This example describes a general procedure for the reduction of azides 6a and 6b (FIG. 1).

To a solution of the azides (4 mmol) in $CH_3OH$ (20 mL) was added 10% Pd/C catalyst (100 mg). The resulting mixture was subjected to hydrogenation by agitation with excess $H_2$(g) at 25 psi in a Parr hydrogenator apparatus at ambient temperature for 3 h. The reaction mixture was filtered through Celite®, and the filtrate was concentrated in vacuo.

Example 11

This example describes the purification of 2-[4,7-bis-(p-toluene-4-sulfonyl)-[1,4,7]triazacyclononan-1-yl]-ethylamine (7a) (FIG. 1).

The residue from Example 10 was purified via column chromatography on neutral alumina eluting with 10% $CH_3OH$-EtOAC. Pure 7a (1.79 g, 93%) was thereby obtained as a colorless oil: $^1$H NMR (CDCl$_3$) δ 2.05–2.43 (m, 6 H), 2.69–2.95 (m, 10 H), 3.25 (s, 4 H), 3.49 (s, 4 H), 7.34 (AB, $J_{AB}$=8.4 Hz, 4 H), 7.65 (AB, $J_{AB}$=8.4 Hz, 4 H); $^{13}$C NMR (CDCl$_3$) δ 21.0 (q), 39.4 (t), 51.6 (t), 52.5 (t), 55.2 (t), 59.8 (t), 126.7 (d), 129.4 (d), 134.8 (s), 143.1 (s). Anal. Calcd for $C_{22}H_{32}N_4S_2O_4$: C, 54.98; H, 6.71. Found: C, 55.00; H, 7.13.

Example 12

This example describes the purification of 3-[4,7-bis-(p-toluene-4-sulfonyl)-[1,4,7]triazacyclononan-1-yl]-propylamine (7b) (FIG. 1).

The residue from Example 10 was purified via column chromatography on neutral alumina eluting with 10% $CH_3OH$-EtOAc. Pure 7b (1.76 g, 91%) was thereby obtained as a colorless oil: $^1$H NMR (CDCl$_3$) δ 1.67 (t, $J_{AB}$=6.2 Hz, 2 H), 1.95 (s, 2 H), 2.48 (s, 6 H), 2.67 (t, $J_{AB}$=5.3 Hz, 2 H), 2.82 (t, $J_{AB}$=5.6 Hz, 2 H), 2.95 (s, 4 H), 3.26 (s, 4 H), 3.53 (s, 4 H), 7.37 (AB, $J_{AB}$=8.2 Hz, 4 H), 7.72 (AB, $J_{AB}$=8.2 Hz, 4 H): $^{13}$C NMR (CDCl$_3$) δ 21.3 (q), 31.2 (t), 40.1 (t), 51.3 (t), 52.4 (t), 54.9 (t), 55.4 (t), 126.9 (d), 129.6 (d), 135.0 (s), 143.3 (s). HRMS (positive ion FAB) Calcd for C$_{23}$H$_{34}$N$_4$S$_2$O$_4$: [M+H]$^+$ m/z 495.2100. Found: [M+H]$^+$ m/z 495.2094. Anal. Calcd for C$_{23}$H$_{34}$N$_4$S$_2$O$_4$(H$_2$O)$_{0.5}$: C, 54.85; H, 7.00. Found: C, 54.47; H, 6.91.

Example 13

This example describes a general procedure for detosylation of 7a and 7b (FIG. 1).

Compound 7a or 7b (1 mmol) was dissolved in concentrated H$_2$SO$_4$ (5 mL) and heated to 115° C. for 72 h under argon. The resulting solution was cooled to ambient temperature and added in portions to diethyl ether (Et$_2$O) (150 mL) at −60° C. The resulting precipitate was collected, washed with Et$_2$O (20 mL), and immediately dissolved in H$_2$O (25 mL). The aqueous solution was extracted with Et$_2$O (10 mL), concentrated to 5 mL, and neutralized with 50% NaOH. The resulting mixture was extracted with CH$_2$Cl$_2$ (3×50 mL), the combined organic layers were dried (MgSO$_4$) and filtered, and the filtrate was concentrated in vacuo.

Example 14

This example describes the purification of 2-[1,4,7]triazacyclononan-1-yl-ethylamine (8a) (FIG. 1).

The crude 8a was obtained in Example 13 as a pale yellow oil (159 mg, 92%): $^1$H NMR (CDCl$_3$) δ 2.27–2.41 (m, 16 H), 3.72 (4 H); $^{13}$C NMR (CDCl$_3$) δ 39.4 (t), 45.8 (t), 46.0 (t), 52.4 (t), 59.7 (t). This material was observed to be unstable; accordingly, it was used immediately as obtained in the next step.

Example 15

This example describes the purification of 3-[1,4,7]triazacyclononan-1-yl-propylamine (8b) (FIG. 1).

The crude 8b was obtained in Example 13 as a colorless, viscous oil (164 mg, 89%): $^1$H NMR (CDCl$_3$) δ 0.94 (t, $J_{AB}$=3.2 Hz, 2 H), 1.48 (s, 4 H), 1.89–2.09 (m, 16 H); $^{13}$C NMR (CDCl$_3$) δ 30.1 (t), 39.0 (t), 45.56 (t), 45.58 (t), 51.9 (t), 54.0 (t). HRMS (positive ion FAB) Calcd for C$_9$H$_{22}$N$_4$: [M+H]$^+$ m/z 187.1923. Found: [M+H]$^+$ m/z 187.1929.

Example 16

This example describes a general procedure for alkylation of tetra-amines 8a and 8b (FIG. 1).

To a suspension of 8a or 8b and K$_2$CO$_3$ in CH$_3$CN under argon was added dropwise tert-butyl bromoacetate, and the resulting mixture was heated at 65° C. for 24 h. The reaction mixture was allowed to cool gradually to ambient temperature, the reaction mixture was filtered, and the filtrate was concentrated in vacuo.

Example 17

This example describes the synthesis of {[3-(4,7-bis-tert-butoxycarbomethyl)-[1,4,7]triazacyclononan-1-yl-ethyl]-tert-butoxycarbonylmethyl-amino]-acetic acid tert-butyl ester (9a).

Compound 8a (500 mg, 2.94 mmol), K$_2$CO$_3$ (913 mg, 11.76 mmol), and tert-butyl bromoacetate (2.86 g, 14.7 mmol) in CH$_3$CN (35 mL) afforded 9a (888 mg, 48%) as a colorless oil after purification by chromatography on silica gel eluting with 5% MeOH—CH$_2$Cl$_2$: $^1$H NMR (CDCl$_3$) δ 1.38–1.72 (m, 36 H), 2.8 (s, 4 H), 3.05–3.73 (m, 20 H); $^{13}$C NMR (CDCl$_3$) δ 27.4 (q), 47.9 (t), 49.3 (t), 50.7 (t), 52.3 (t), 53.6 (t), 55.2 (t), 56.2 (t), 81.2 (s), 81.3 (s), 169.5 (s), 169.8 (s). HRMS (positive ion FAB) Calcd for C$_{32}$H$_{60}$N$_4$O$_8$: [M+H]$^+$ m/z 629.4489. Found: [M+H]$^+$ m/z 629.4479.

Example 18

This example describes the purification of {[3-(4,7-bis-tert-butoxycarbomethyl)-[1,4,7]triazacyclononan-1-yl-propyl]-tert-butoxycarbonylmethyl-amino]-acetic acid tert-butyl ester (9b) (FIG. 1).

Compound 8b (360 mg, 1.95 mmol), K$_2$CO$_3$ (1.08 g, 7.80 mmol), and tert-butyl bromoacetate (1.52 g, 7.82 mmol) in CH$_3$CN (23 mL) afforded 9b (652 mg, 52%) as a colorless oil after purification by chromatography on silica gel eluting with 4% CH$_3$OH—CH$_2$Cl$_2$:$^1$H NMR (CDCl$_3$) δ 1.21–1.62 (m, 36 H), 2.00 (s, 2 H), 2.60–2.95 (m, 6 H), 3.03–3.84 (m, 18 H); $^{13}$C NMR (CDCl$_3$) δ 22.7 (t), 27.9 (q), 49.2 (t), 51.4 (t), 52.0 (t), 52.7 (t), 54.1 (t), 55.9 (t), 57.7 (t), 81.1 (s), 81.3 (s), 170.2 (s), 170.4 (s). HRMS (positive ion FAB) Calcd for C$_{33}$H$_{62}$N$_4$O$_8$: [M+H]$^+$ m/z 643.4646. Found: [M +H]$^+$ m/z 642.4641.

Example 19

This example describes the deprotection of tetra-tert-butyl esters 9a and 9b (FIG. 1).

A solution of either 9a or 9b in dry 1,4-dioxane cooled in an ice-water bath was saturated with HCl (g) for 4 h, after which the mixture was allowed to return to ambient temperature and then stirred for 12 h. The precipitate was collected, washed with ethyl ether, and dissolved into water. The solution was then lyophilized to give 1 or 2 (FIG. 1) as a pale yellow solid.

Example 20

This example describes the synthesis of {[2-(4,7-bis-carboxymethyl)-[1,4,7]triazacyclononan-1-yl-ethyl]-carbonylmethyl-amino]-acetic acid tetrahydrochloride (1) (FIG. 1).

Compound 9a (130 mg, 0.21 mmol) in 1,4-dioxane (20 mL) afforded 1 (78 mg, 92%) as a salt: $^1$H NMR (CDCl$_3$) δ 3.21–3.45 (m, 10 H), 3.75–3.93 (m, 8 H), 4.63–4.78 (m, 8 H); $^{13}$C NMR (CDCl$_3$) δ 49.6 (t), 50.7 (t), 51.2 (t), 51.6 (t), 55.6 (t), 56.9 (t), 169.7 (s), 170.2 (s). MS (positive ion FAB) [M+H]$^+$ m/e 405. Anal. Calcd for C$_{16}$H$_{28}$N$_4$O$_8$(HCl)$_4$(H$_2$O)$_4$: C, 30.88; H, 6.48. Found: C, 30.71; H, 6.38.

Example 21

This example describes the synthesis of {[3-(4,7-bis-carboxymethyl)-[1,4,7]triazacyclononan-1-yl-propyl]-carbonyl-methylamino]-acetic acid tetrahydrochloride (2) (FIG. 1).

Compound 9b (280 mg, 0.44 mmol) in 1,4-dioxane (30 mL) afforded 2 (162 mg, 88%) as a salt: $^1$H NMR (D$_2$O, pD=1) δ 3.23–3.62 (m, 8 H), 3.90 (s, 4 H), 4.21 (s, 4 H), 4.81 (s, 10 H); $^{13}$C NMR (D$_2$O, pD=1) δ 49.3 (t), 50.3 (t), 52.7 (t), 54.0 (t), 54.3 (t), 56.0 (t), 167.4 (s), 171.1 (s). MS (positive ion FAB) m/e 419 [M+H]$^+$. Anal. Calcd for C$_{17}$H$_{30}$N$_4$O$_8$(HCl)$_4$(H$_2$O): C, 35.07; H, 6.23. Found: C, 35.45; H, 6.15.

Example 22

This example describes the synthesis of radiolabeled 1 and 2 (FIG. 1) and the stability of 1 and 2 in serum.

The $^{88}$Y complexes of 1 and 2 were prepared by the addition of 350 µCi of $^{88}$Y (0.1 M HCl adjusting the pH to 4.5 with 5 M NH$_4$OAc) to 20 µL of 0.2 M ligand solution in 0.15 M NH$_4$OAc of pH 4.5. The reactions were forced to completion by heating the reaction mixture at 80° C. for 18 h, after which they were loaded onto a column of Chelex-100 resin (1 mL volume bed, equilibrated with 0.15 M NH$_4$OAc). The complexes were eluted from the resin with 0.15 M NH$_4$Ac, while the resin retained the free $^{88}$Y.

The stability of the corresponding $^{88}$Y-labeled complexes formed with chelators 1 and 2 in human serum was assessed by measuring the release of $^{88}$Y from the complexes at 37° C. over 14 days. The pH of the $^{88}$Y complex solutions was adjusted to 7.0 with PBS buffer and 250 µCi of either complex were added to 1 mL of human serum incubated at 37° C. An aliquot of the serum (5–10 µL) was taken at selected times and analyzed by SE-HPLC with a TSK-3000 column eluted with PBS at a 1 mL/min flow rate. The serum stability of the $^{88}$Y complexes was assessed by measuring the release of $^{88}$Y radionuclide from the complexes to serum proteins. The results are shown in FIG. 2, which is a line graph of $^{88}$Y (%) vs. time (d), in which ♦ represents the serum stability of $^{88}$Y-1 and ■ represents the serum stability of $^{88}$Y-2.

Figure 2:
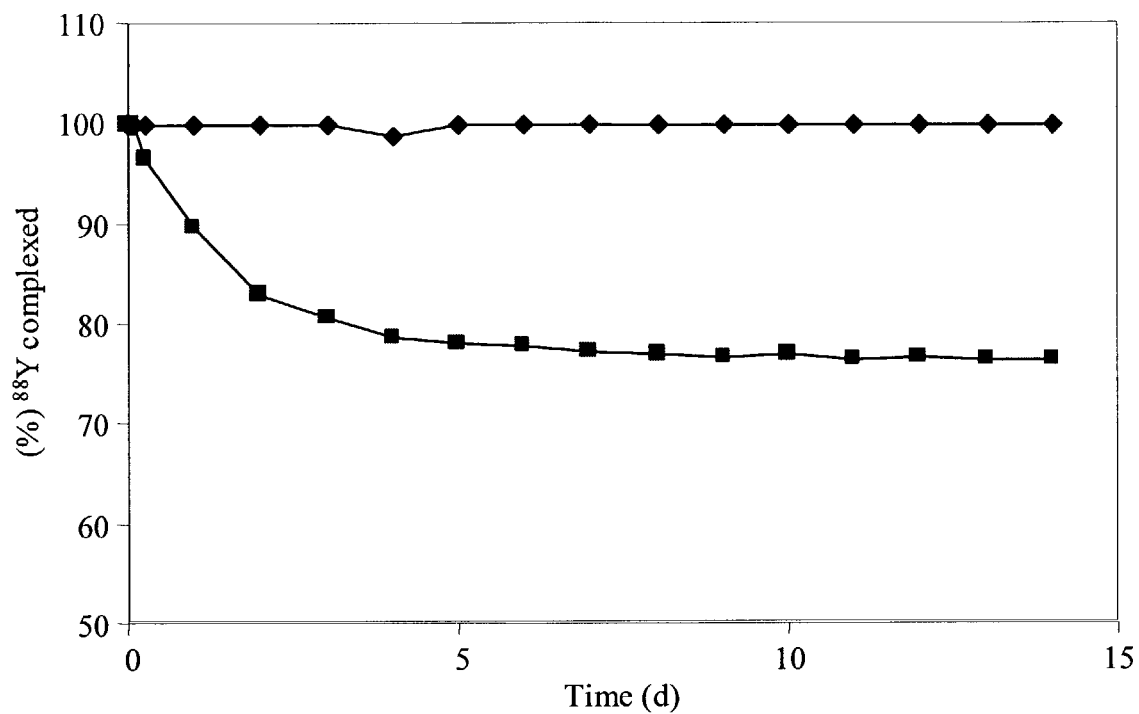
FIG. 2 is a line graph of complexed $^{88}$Y (%) vs. time (d), which illustrates the serum stability of $^{88}$Y-1 (♦) and $^{88}$Y-2 (■) at pH 7 and 37° C.

The results in FIG. 2 show that $^{88}$Y-labeled ligand 1 having an ethylene-bridge is stable in serum for up to 14 days with no measurable loss of radioactivity. However, considerable release of radioactivity was observed from the $^{88}$Y chelate formed with 2, which possesses the longer propylene bridge. The percentage of $^{88}$Y released from this complex at 14 days was about 25%. It seems likely that the stability of the Y(III) radiolabeled complex in serum is dependent on the length of the carbon chain between the pendant donor groups and the macrocyclic ring. The observed release of radioactivity from the chelate 2 might also be a consequence of the formation of a six-membered chelate ring as opposed to what is generally considered to be the more stable arrangement of donors, i.e., a five-membered chelate ring for complexation of Y(III).

Example 23

This example describes the formation kinetics of radiolabeled 1, 2 (FIG. 1) and DOTA.

Formation kinetics of Y(III) complexes of 1, 2, and DOTA (Macrocyclics) was measured by monitoring the absorption at 652 nm. To 2 mL of 1.6 mM YCl$_3$ (from atomic absorption standard solution, Aldrich) and 5 mM Arsenazo III (Sigma) in 0.15 M NH$_4$OAc (pH 4.0, metal-free), 20 µL of 10 mM ligand solution were added into a cell. After mixing (<5 sec), absorption of the solution at 652 nm (absorption wavelength of Y(III)-Arsenazo III) (Kline et al., *Bioconjugate Chem.*, 1991, 2, 26–31) was immediately followed over time at room temperature using an HP 8452A Diode Array Spectrophotometer, which was pre-blanked with a 5 mM Arsenazo III solution. Without any ligand added, the absorption was 0.089 for 1.6 mM YCl$_3$ in 5 mM Arsenazo III solution at 652 nm.

Example 24

This example demonstrates the complexation kinetics of metal complexes of 1, 2 (FIG. 1) and DOTA as prepared in Example 22.

Figure 3:
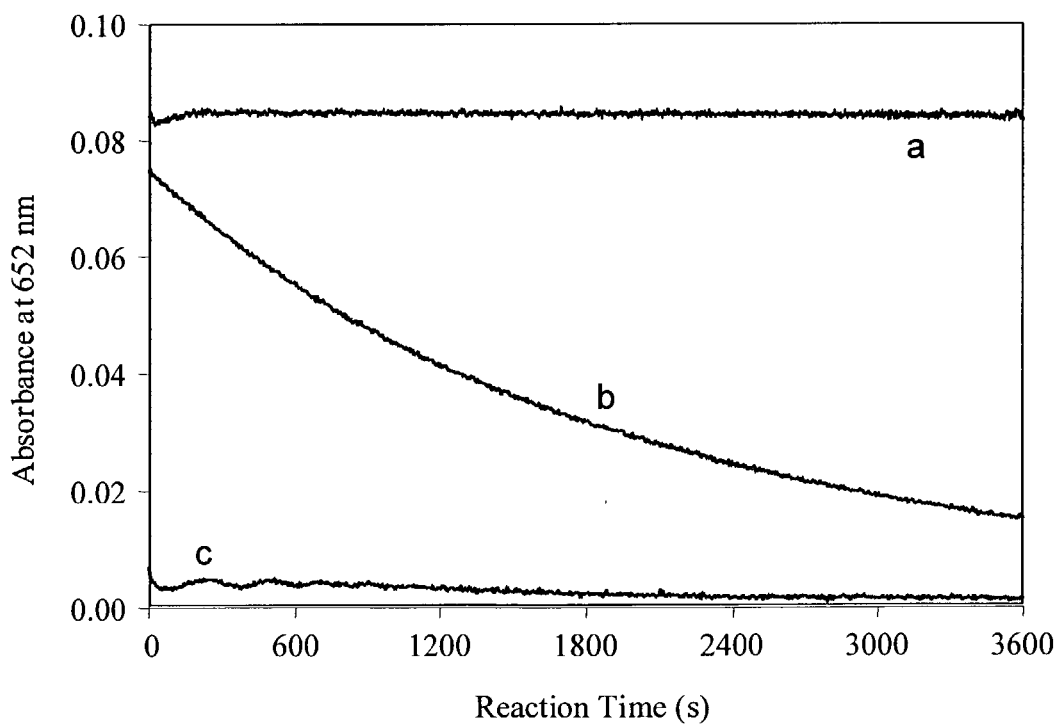
FIG. 3 is a line graph of absorbance at 652 nm vs. reaction time (s) for Y-1 (curve c), Y-2 (curve a), and Y-DOTA (curve b) at pH 4 and 25° C.

The complexation kinetics of novel chelates 1, 2 and DOTA with Y(III) was qualitatively investigated using a competing reaction with Arsenazo III according to a modification of a previously reported procedure (Kodama et al., *Inorg. Chem.*, 1991, 30, 1270–1273). The absorbance ($A_{652}$) for the Y(III)-Arsenazo III complex was measured in the absence and in the presence of the chelates (1, 2, and DOTA) over 1 h. The results are shown in FIG. 3, which is a line graph of absorbance at 652 nm vs. reaction time (s), in which curve "a" represents Y-2, "b" represents Y-DOTA, and curve "c" represents Y-1. The results indicate that the complex formation of ligand 1 with Y (III) (curve "c" in FIG. 3) is quite rapid and is essentially complete very shortly after the starting point of measurement. However, ligand 2 (curve "a" in FIG. 3) displays very slow complexation of Y(III) as compared to 1. Furthermore, the degree of complexation of 2 was slight and remained unchanged over the period of measurement. Complexation of Y(III) by 2 is assumed to occur to some degree, but the formed complex might undergo decomplexation due to an absence of complex stability, ultimately leading to an unfavorable equilibrium situation. This interpretation also agrees with the serum stability result of the $^{88}$Y-labeled complex with 2, which displayed a significant loss of radio-yttrium in serum. As expected, DOTA displayed sluggish complexation with Y(III) (curve "b" in FIG. 3). The time scan measurements obviously show that 1 does form a complex with Y(III) at a much greater rate than DOTA with comparable in vitro stability.

Example 25

This example demonstrates the in vivo biodistribution of metal complexes of 1 (FIG. 1) and DOTA as prepared in Example 22.

Female Balb/c mice were obtained from Charles River Laboratories (Wilmington, Mass.) at 4–6 weeks of age. The pH of the $^{86}$Y-labeled ligands was adjusted to pH ~7.0 with 0.5 M sodium bicarbonate (pH 10.5) and diluted in PBS. The radiolabeled ligands (5.9 µCi of $^{86}$Y-DOTA, 5.0 µCi of $^{86}$Y-1) were administered to the mice in 200 µL volumes via tail vein injection. The mice (5 per data point) were sacrificed by exsanguination at 0.5 h, 1 h, 4 h, 8 h, and 24 h. Blood and the major organs were harvested and wet-weighed, and the radioactivity was measured in a γ-scintillation counter (Minaxi-γ; Packard, Downers Grove, Ill.). The % ID/g was determined for each tissue. The values presented are the mean and standard error of the mean for each tissue. All animal experiments were performed in compliance with current regulations and guidelines of the U.S. Dept. of Agriculture and the NIH Animal Research Advisory Committee.

Figure 4:
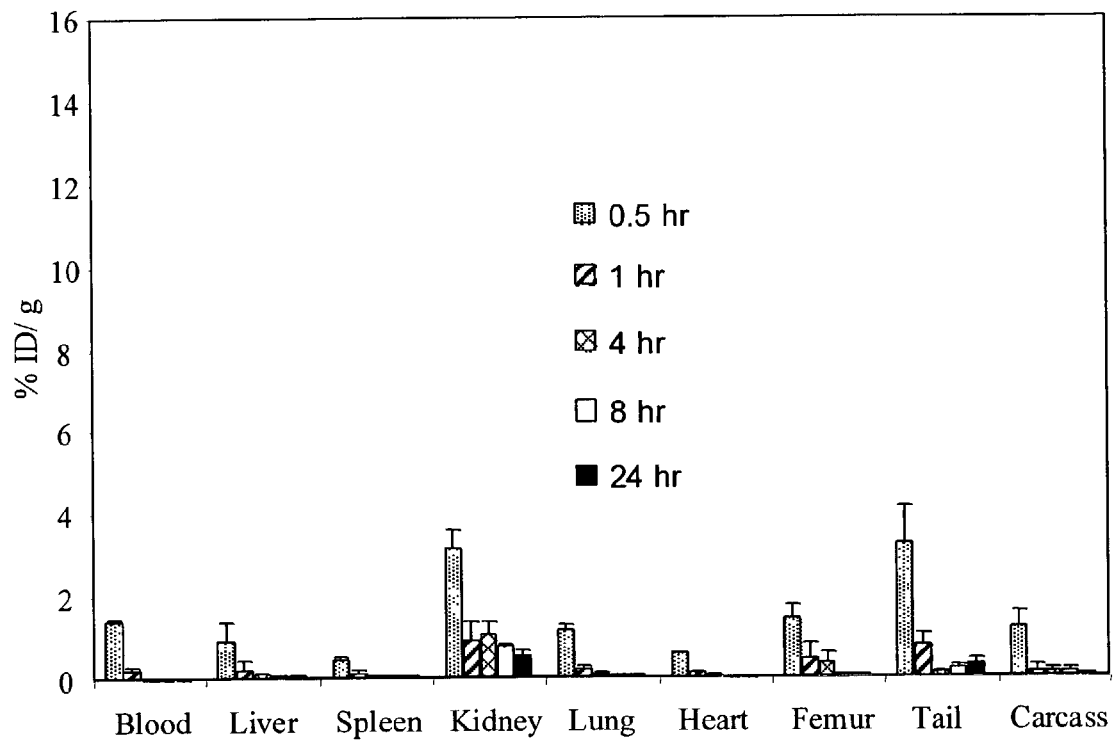
FIG. 4 is a bar graph of % ID/g vs. sample source, which illustrates the biodistribution of $^{86}$Y-1 in Balb/c mice following intravenous (i.v.) injection.
Figure 5:
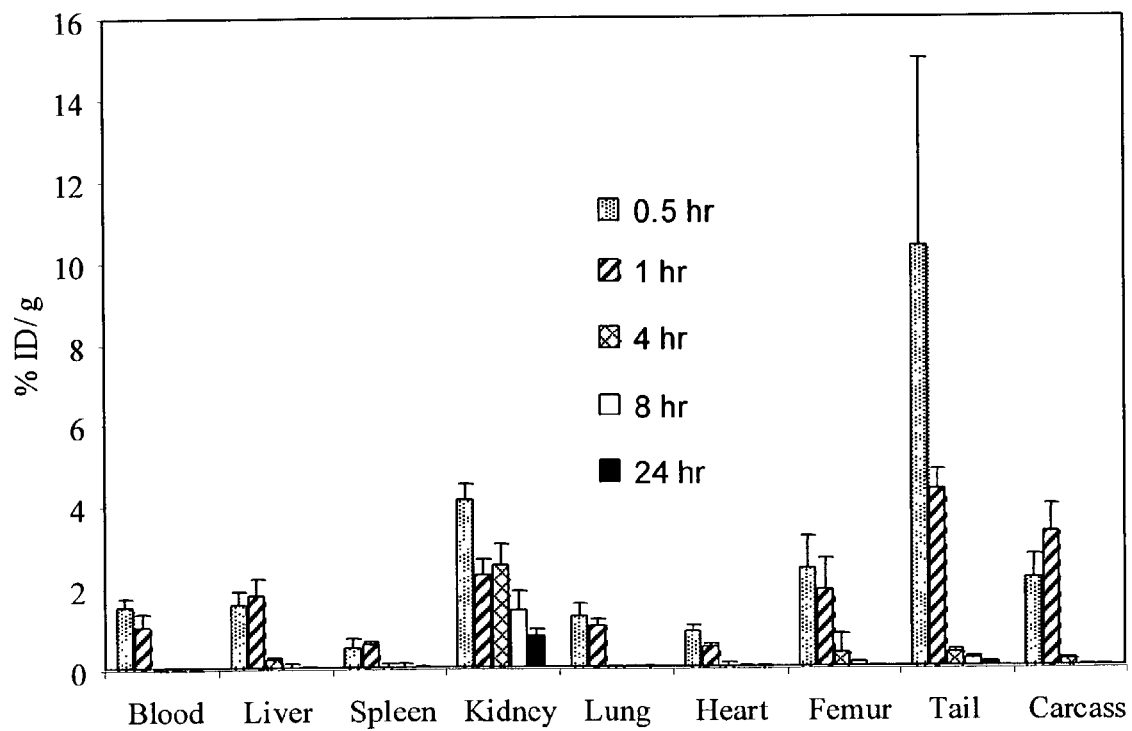
FIG. 5 is a bar graph of % ID/g vs. sample source, which illustrates the biodistribution of $^{86}$Y-DOTA in Balb/c mice following i.v. injection.

In order to evaluate the in vivo stability of $^{86}$Y-labeled ligand 1, which displayed excellent serum stability and kinetics, a biodistribution study was performed in mice. For the purpose of comparison, a biodistribution of $^{86}$Y-labeled DOTA in mice was also performed. The results of the biodistribution studies for $^{86}$Y-1 and $^{86}$Y-DOTA are shown in FIGS. 4 and 5, respectively. FIG. 4 is a bar graph of % ID/g vs. selected organs, which illustrates the biodistribution of $^{86}$Y-1 in Balb/c mice following i.v. injection. FIG. 5 is a bar graph of % ID/g vs. selected organs, which illustrates the biodistribution of $^{86}$Y-DOTA in Balb/c mice following i.v. injection. Radioactivity that accumulated in selected organs and cleared from the blood of mice was measured at five time points: 0.5 h, 1 h, 4 h, 8 h, and 24 h post-injection of the two $^{86}$Y-labeled complexes.

The data in FIGS. 4 and 5 show that the accumulated radioactivity in the organs at 4 h post-injection of the complexes is negligible for both $^{86}$Y-1 and $^{86}$Y-DOTA. Both $^{86}$Y-1 and $^{86}$Y-DOTA display a slightly higher radioactivity level in the kidney as compared to that in other organs, no doubt associated with whole body clearance and elimination of these complexes. At 24 h, radioactivity that accumulated in kidney was 0.54±0.13 percent injected dose per gram (% ID/gm) and 0.84±0.16 % ID/gm for $^{86}$Y-1 and $^{86}$Y-DOTA, respectively. The data in FIGS. 4 and 5 also indicate a rapid blood clearance for $^{86}$Y-1 and $^{86}$Y-DOTA. The $^{86}$Y-1 displayed low bone-uptake that peaked at 1.47±0.28 % ID/gm at 0.5 h to decline to 0.05±0.01 % ID/gm at 24 h. This trend is a noteworthy result in that free yttrium is known to be efficiently deposited at the bone (Jowsey et al., *Radiation Res.*, 1958, 8, 490–501). As compared to that of complex $^{86}$Y-1, the bone accumulation of $^{86}$Y-DOTA was actually slightly higher at all time points. The results of the biodistribution studies as a whole indicate that $^{86}$Y-1 displays comparable in vivo stability to $^{86}$Y-DOTA.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of the formula (Ia):

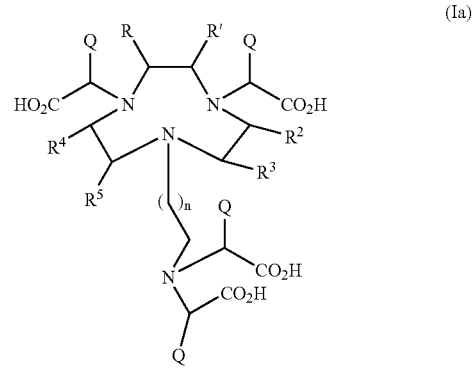

wherein each of R, R', $R^{2-5}$ and Q are independently hydrogen, alkyl, cycloalkyl, alkoxy, hydroxyalkyl, aryl, aryloxy, hydroxyaryl, heteroaryl, thioalkyl, thioaryl, or an amino acid-containing group; or wherein R and R' together form a cycloalkyl; and n is 1 or 2, with the proviso that when all of R, R', and $R^{2-5}$ are H, at least one Q is not H.

2. A compound of the formula (Ib):

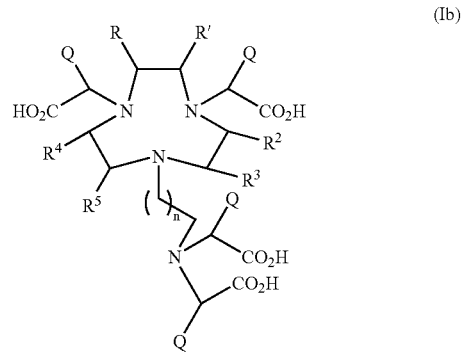

wherein one of R, R', $R^{2-5}$ and Q is selected from the group consisting of alkyl, cycloalkyl, alkoxy, hydroxyalkyl, aryl, aryloxy, hydroxyalkyl, heteroaryl, thioalkyl, thioaryl, and an amino acid-containing group or wherein R and R' together form a cycloalkyl; and the remaining substituents are each independently hydrogen, alkyl, cycloalkyl, alkoxy, hydroxyalkyl, aryl, aryloxy, hydroxyaryl, heteroaryl, thioalkyl, thioaryl, or an amino acid-containing group; or wherein R and R' together form a cycloalkyl; and n is 1 or 2.

3. A compound of the formula (II):

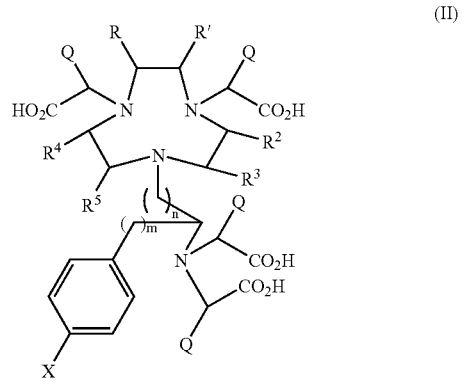

wherein each of R, R', $R^{2-5}$ and Q are independently hydrogen, alkyl, cycloalkyl alkoxy, hydroxyalkyl, aryl, aryloxy, hydroxyaryl, heteroaryl, thioalkyl, thioaryl, or an amino acid-containing group; or wherein R and R' together form a cycloalkyl; X is hydrogen, halo, alkyl, hydroxy, nitro, amino, alkylamino, thiocyano, isothiocyano, carboxyl, carboxyalkyl, carboxyalkyloxy, amido, alkylamido, or haloalkylamido; n is 1 or 2; and m is 1–5.

4. A complex comprising the compound of claim 1 and a metal ion, wherein the metal ion is optionally radioactive, or a radioactive isotope of carbon, nitrogen, iodine, fluorine, oxygen, or helium.

5. A complex comprising the compound of claim 2 and a metal ion, wherein the metal ion is optionally radioactive, or a radioactive isotope of carbon, nitrogen, iodine, fluorine, oxygen, or helium.

6. A complex comprising the compound of claim 3 and a metal ion, wherein the metal ion is optionally radioactive, or a radioactive isotope of carbon, nitrogen, iodine, fluorine, oxygen, or helium.

7. The complex of claim 4, wherein the metal ion is selected from the group consisting of Bi, Pb, Y, Te, Mn, Cr, Fe, Co, Ni, Tc, In, Ga, Cu, Re, a lanthanide, and an actinide.

8. The complex of claim 5, wherein to metal ion is selected from the group consisting of Bi, Pb, Y, Te, Mn, Cr, Fe, Co, Ni, Tc, In, Ga, Cu, Re, a lanthanide, and an actinide.

9. The complex of claim 6, wherein the metal ion is selected from the group consisting of Bi, Pb, Y, Te, Mn, Cr, Fe, Co, Ni, Tc, In, Ga, Cu, Re, a lanthanide, and an actinide.

10. The complex of claim 7 wherein the lanthanide is Gd(III).

11. The complex of claim 8, wherein the lanthanide is Gd(III).

12. The complex of claim 9, wherein the lanthanide is Gd(III).

13. A pharmaceutical composition comprising pharmaceutically acceptable carrier and the compound of claim 1.

14. A pharmaceutical composition comprising a pharmaceutically acceptable carrier and the compound of claim 2.

15. A pharmaceutical composition comprising a pharmaceutically acceptable carrier and the compound of claim 3.

16. A pharmaceutical composition comprising a pharmaceutically acceptable carrier and the complex of claim 4.

17. A pharmaceutical composition comprising a pharmaceutically acceptable carrier and the complex of claim 5.

18. A pharmaceutical composition comprising a pharmaceutically acceptable carrier and the complex of claim 6.

19. A method for diagnostic imaging of a host, which method comprises:
  (i) administering to the host a complex of claim 4 in an amount effective to provide an image; and
  (ii) exposing the host to an energy source, whereupon a diagnostic image of the host is obtained.

20. A method for diagnostic imaging of a host, which method comprises:
  (i) administering to the host a complex of claim 5 in an amount effective to provide an image; and
  (ii) exposing the host to an energy source, whereupon a diagnostic image of the host is obtained.

21. A method for diagnostic imaging of a host, which method comprises:
  (i) administering to the host a complex of claim 6 in an amount effective to provide an image; and
  (ii) exposing the host to an energy source, whereupon a diagnostic image of the host is obtained.

22. The method of claim 19, wherein the diagnostic image is selected from the group consisting of a magnetic resonance image, an x-ray contrast image and a single photon emission computed spectroscopy (SPECT) image.

23. The method of claim 20, wherein the diagnostic image is selected from the group consisting of a magnetic resonance image, an x-ray contrast image and a single photon emission computed spectroscopy (SPECT) image.

24. The method of claim 21, wherein the diagnostic image is selected from the group consisting of a magnetic resonance image, an x-ray contrast image and a single photon emission computed spectroscopy (SPECT) image.

25. A method for magnetic resonance imaging of a host, which method comprises:
  (i) administering to the host a complex of claim 4, in which the metal ion is paramagnetic, in an amount effective to provide an image; and
  (ii) exposing the host to a magnet, whereupon a magnetic resonance image of the host is obtained.

26. A method for magnetic resonance imaging of a host, which method comprises:
  (i) administering to the host a complex of claim 5, in which the metal ion is paramagnetic, in an amount effective to provide an image; and
  (ii) exposing the host to a magnet, whereupon a magnetic resonance image of the host is obtained.

27. A method for magnetic resonance imaging of a host, which method comprises:
  (i) administering to the host a complex of claim 6, in which the metal ion is paramagnetic, in an amount effective to provide an image; and
  (ii) exposing the host to a magnet, whereupon a magnetic resonance image of the host is obtained.

28. A method for x-ray imaging of a host, which method comprises:
  (i) administering to the host a complex of claim 4, in which the metal ion is radio-opaque, in an amount effective to provide an image; and
  (ii) exposing the host to x-rays, whereupon an x-ray contrast image of the host is obtained.

29. A method for x-ray imaging of a host, which method comprises:
  (i) administering to the host a complex of claim 5, in which the metal ion is radio-opaque, in an amount effective to provide an image; and
  (ii) exposing the host to x-rays whereupon an x-ray contrast image of the host is obtained.

30. A method for x-ray imaging of a host, which method comprises:
  (i) administering to the host a complex of claim 6, in which the metal ion is radio-opaque, in an amount effective to provide an image; and
  (ii) exposing the host to x-rays whereupon an x-ray contrast image of the host is obtained.

31. A method for single photon emission computed spectroscopy (SPECT) imaging, which method comprises:
  (i) administering to the host a complex of claim 4, in which the metal emits a single photon, in an amount effective to provide an image; and
  (ii) exposing the host to an energy source, whereupon a SPECT image of the host is obtained.

32. A method for single photon emission computed spectroscopy (SPECT) imaging, which method comprises:
  (i) administering to the host a complex of claim 5, in which the metal emits a single photon, in an amount effective to provide an image; and
  (ii) exposing the host to an energy source, whereupon a SPECT image of the host is obtained.

33. A method for single photon emission computed spectroscopy (SPECT) imaging, which method comprises:
(i) administering to the host a complex of claim 6, in which the metal emits a single photon, in an amount effective to provide an image; and
(ii) exposing the host to an energy source, whereupon a SPECT image of the host is obtained.

34. A method for treating cancer in a mammal, which method comprises administering to the mammal a complex of claim 4 in an amount effective to treat cancer, wherein the cancer is selected from the group consisting of lymphomas, leukemias, colo-rectal cancer, ovarian cancer, breast cancer, and prostate cancer.

35. A method for treating cancer in a mammal, which method comprises administering to the mammal a complex of claim 5 in an amount effective to treat cancer, wherein the cancer is selected from the group consisting of lymphomas, leukemias, colo-rectal cancer, ovarian cancer, breast cancer, and prostate cancer.

36. A method for treating cancer in a mammal, which method comprises administering to the mammal a complex of claim 6 in an amount effective to treat cancer, wherein the cancer is selected from the group consisting of lymphomas, leukemias, colo-rectal cancer, ovarian cancer, breast cancer, and prostate cancer.

37. The method of claim 25, wherein the complex comprises Gd.

38. The method of claim 26, wherein the complex comprises Gd.

39. The method of claim 27, wherein the complex comprises Gd.

40. The method of claim 28, wherein the complex comprises $^{111}$In.

41. The method of claim 29, wherein the complex comprises $^{111}$In.

42. The method of claim 30, wherein the complex comprises $^{111}$In.

43. The method of claim 34, wherein the complex comprises $^{90}$Y.

44. The method of claim 35, wherein the complex comprises $^{90}$Y.

45. The method of claim 36, wherein the complex comprises $^{90}$Y.

46. The method of claim 34, wherein the complex comprises $^{213}$Bi.

47. The method of claim 35, wherein the complex comprises $^{213}$Bi.

48. The method of claim 36, wherein the complex comprises $^{213}$Bi.

49. The compound of claim 1, wherein R and R' are methyl or together form a cycloalkyl.

50. The compound of claim 2, wherein R and R' are methyl or together form a cycloalkyl.

51. The compound of claim 3, wherein R and R' are methyl or together form a cycloalkyl.

52. The complex of claim 4, wherein R and R' are methyl or together form a cycloalkyl.

53. The complex of claim 5, wherein R and R' are methyl or together form a cycloalkyl.

54. The complex of claim 6, wherein R and R' are methyl or together form a cycloalkyl.

55. The pharmaceutical composition of claim 13, wherein R and R' are methyl or together form a cycloalkyl.

56. The pharmaceutical composition of claim 14, wherein R and R' are methyl or together form a cycloalkyl.

57. The pharmaceutical composition of claim 15, wherein R and R' are methyl or together form a cycloalkyl.

58. The pharmaceutical composition of claim 16, wherein R and R' are methyl or together form a cycloalkyl.

59. The pharmaceutical composition of claim 17, wherein R and R' are methyl or together form a cycloalkyl.

60. The pharmaceutical composition of claim 18, wherein R and R' are methyl or together form a cycloalkyl.

61. The method of claim 34, wherein R and R' are methyl or together form a cycloalkyl.

62. The method of claim 35, wherein R and R' are methyl or together form a cycloalkyl.

63. The method of claim 36, wherein R and R' are methyl or together form a cycloalkyl.

* * * * *